United States Patent
Xue et al.

(10) Patent No.: US 12,428,656 B2
(45) Date of Patent: Sep. 30, 2025

(54) NITRILASE MUTANT AND APPLICATION THEREOF IN THE SYNTHESIS OF 1-CYANOCYCLOHEXYL ACETIC ACID

(71) Applicant: ZHEJIANG UNIVERSITY OF TECHNOLOGY, Zhejiang (CN)

(72) Inventors: Yaping Xue, Zhejiang (CN); Neng Xiong, Zhejiang (CN); Qian Li, Zhejiang (CN); Yuguo Zheng, Zhejiang (CN)

(73) Assignee: ZHEJIANG UNIVERSITY OF TECHNOLOGY, Hangzhou (CN)

( * ) Notice: Subject to any disclaimer, the term of this patent is extended or adjusted under 35 U.S.C. 154(b) by 719 days.

(21) Appl. No.: 17/603,864

(22) PCT Filed: Dec. 11, 2020

(86) PCT No.: PCT/CN2020/135582
§ 371 (c)(1),
(2) Date: Oct. 14, 2021

(87) PCT Pub. No.: WO2021/169490
PCT Pub. Date: Sep. 2, 2021

(65) Prior Publication Data
US 2022/0372531 A1 Nov. 24, 2022

(30) Foreign Application Priority Data
Feb. 28, 2020 (CN) .......................... 202010127927.7

(51) Int. Cl.
*C12P 13/00* (2006.01)
*C12N 1/20* (2006.01)
*C12N 9/78* (2006.01)
*C12N 15/70* (2006.01)
*C12R 1/19* (2006.01)

(52) U.S. Cl.
CPC ............ *C12P 13/002* (2013.01); *C12N 1/205* (2021.05); *C12N 9/78* (2013.01); *C12N 15/70* (2013.01); *C12Y 305/05001* (2013.01); *C12N 2800/101* (2013.01); *C12R 2001/19* (2021.05)

(58) Field of Classification Search
None
See application file for complete search history.

(56) References Cited

FOREIGN PATENT DOCUMENTS

| CN | 101629192 A | 1/2010 |
|---|---|---|
| CN | 102911975 A | 2/2013 |
| CN | 104212784 A | 12/2014 |
| CN | 107177576 A | 9/2017 |
| CN | 108486088 A | 9/2018 |
| CN | 111471668 A | 7/2020 |
| WO | WO-2006/069110 A2 | 6/2006 |

OTHER PUBLICATIONS

Xu, Zhe, et al. "Engineering the residues on "A" surface and C-terminal region to improve thermostability of nitrilase." Enzyme and microbial technology 113 (2018): 52-58. (Year: 2018).*
Xu, Zhe, et al. "Highly efficient conversion of 1-cyanocycloalkaneacetonitrile using a "super nitrilase mutant"." Bioprocess and biosystems engineering 42 (2019): 455-463. (Year: 2019).*
UniProt, Aliphatic nitrilase, Rhizobium multihospitium, https://www.uniprot.org/uniprotkb/A0A1C3XDR2/entry (Year: 2016).*
K Singh, Raushan, et al. "Protein engineering approaches in the post-genomic era." Current Protein and Peptide Science 18 (2017): 1-11. (Year: 2017).*
Zhang, Meiling, David A. Case, and Jeffrey W. Peng. "Propagated perturbations from a peripheral mutation show interactions supporting WW domain thermostability." Structure 26.11 (2018): 1474-1485. (Year: 2018).*
Abd Rahim, Siti Noraida, et al. "Effect of agitation speed for enzymatic hydrolysis of tapioca slurry using encapsulated enzymes in an enzyme bioreactor." International Journal of Chemical Engineering and Applications 6.1 (2015): 38. (Year: 2015).*
Bornhorst JA, Falke JJ. Purification of proteins using polyhistidine affinity tags. Methods Enzymol. 2000;326:245-54. doi: 10.1016/s0076-6879(00)26058-8. PMID: 11036646; PMCID: PMC2909483. (Year: 2000).*
Dialysis Methods https://www.thermofisher.com/ca/en/home/life-science/protein-biology/protein-biology-learning-center/protein-biology-resource-library/pierce-protein-methods/dialysis-methods-protein-research.html#:~:text=Note%3A%20For%20best%20results%2C%20use,it%20is%20changed%20several%20times. (Year: 2019).*

* cited by examiner

*Primary Examiner* — Anand U Desai
(74) *Attorney, Agent, or Firm* — Muncy, Geissler, Olds & Lowe, P.C.

(57) ABSTRACT

The present invention provides a nitrilase mutant and application thereof in the synthesis of 1-cyanocyclohexyl acetic acid, the nitrilase mutant is obtained by mutating one or two of the amino acids at position 180 and 205 of the amino acid sequence shown in SEQ ID No. 2. In the present invention, by semi-rational design and protein molecular modification, the specific enzyme activity of the nitrilase double mutant AcN-G180D/A205C was increased by up to 1.6 folds, and the conversion rate>99%. And the reaction time was shortened to a quarter of the original using the recombinant *Escherichia coli* containing the nitrilase mutant to hydrolyze 1-cyanocyclohexylacetonitrile at high temperature (50° C.). Therefore, the mutants obtained by the present invention have a good application prospect in efficiently catalyzing 1-cyanocyclohexylacetonitrile to synthesize gabapentin intermediate, 1-cyanocyclohexyl acetic acid.

7 Claims, 6 Drawing Sheets
Specification includes a Sequence Listing.

NITRILASE MUTANT AND APPLICATION THEREOF IN THE SYNTHESIS OF 1-CYANOCYCLOHEXYL ACETIC ACID

The instant application contains a Sequence Listing which has been submitted electronically in the ASCII text file and is hereby incorporated by reference in its entirety. The ASCII text file is a sequence listing entitled "2022 Jan. 7-Seq-Listing" created on Jan. 7, 2022 and having a size of 24,372 bytes in compliance of 37 CFR 1.821.

TECHNICAL FIELD

The present invention relates to a nitrilase mutant derived from Acidovorax *facilis* CCTCC NO: M 209044 and its application in the synthesis of an antiepileptic drug, gabapentin.

BACKGROUND ART

Gabapentin was developed by Warner-Lambert Company, USA, and first listed in the UK in May 1993. Gabapentin can prevent convulsions induced by some chemicals (such as picrotoxin, bicuculine, strychnine) and non-chemical stimuli (such as sound source, electric shock), and has curative effect on partial seizures and secondary generalized tonic-clonic seizures. Compared with similar products currently used, it has fast oral absorption, good tolerance, less toxic and side effects, and good therapeutic effect. It is not metabolized in vivo, does not bind to plasma proteins, does not induce liver enzymes, and can pass through the blood-brain barrier of human brains. It is very unlikely to interact with other anti-epileptic drugs, it is thus particularly effective as a superposition drug of intractable epilepsy.

1-Cyanocyclohexyl acetic acid is a key intermediate for synthesis of a new generation of the anti-epileptic drug, gabapentin, the market prospect is very broad. At present, all the synthesis methods of gabapentin and its key intermediate 1-cyanocyclohexyl acetic acid adopt chemical synthesis technology, and there are problems of serious environmental pollution, serious corrosion to equipment, and great danger, etc. in the production process.

Nitrilase (Nitrilase EC 3.5.5.1) is an important industrial enzyme that is able to hydrolyze nitrile (containing —CN) to the corresponding carboxylic acid and ammonia. Cyano hydrolysis reaction accomplished by nitrilase avoids the conditions such as high temperature or strong acid and alkali which are required in the chemical synthesis process, greatly reduces the generation of by-products and waste, and reflects high selectivity, high efficiency and environmental economy and meets the requirements of green chemistry. At present, there are many examples of the application of nitrilase in the synthesis of pharmaceutical intermediates.

The Swiss company Lonza was the first company to use nitrilase to catalyze the production of niacin and also used the combined action of nitrilase and nicotinamide dehydrogenase to degrade the substrates 2-cyanopyridine and 2-cyanopyrazine into the drug intermediates 5-hydroxypyridine-2-carboxylic acid and 5-hydroxypyrazine-2-carboxylic acid, respectively. The reaction selectivity was high, and the conversion rate was close to 100%, which has a great advantage compared with traditional chemical methods. Shanghai Pesticide Research Institute Co., Ltd. and Zhejiang Qianjiang Biochemical Co., Ltd. cooperated to construct a genetically engineered strain *E. coli* BL21 (DE3)-pETNY Nitd with high-activity nitrilase that could catalyze the conversion of hydroxyacetonitrile to glycolic acid. The concentration of glycolic acid after the conversion of wild strains for 72 h reached 11.6%, whereas the concentration of glycolic acid after the conversion of the genetically engineered strain for 20 h reached 36%, the catalytic efficiency was significantly improved. Banerjee et al. recombinantly expressed the *P. putida* MTCC 5110 nitrilase gene in *E. coli*, and systematically optimized the enzyme production conditions. The recombinant enzyme showed high nitrilase activity to mandelonitrile, and the final conversion results showed that the yield and ee value of (R)-mandelic acid reached 87% and 99.99%, respectively. Chauhan et al. obtained a nitrilase encoding gene of Acidovorax *facilis* 72 W by amplification, and overexpressed it in *E. coli*. The recombinant enzyme has high stereoselectivity to aliphatic dinitriles and could convert 2-methylglutaronitrile to 4-cyanovaleric acid, the substrate conversion rate reached 100%, no amide compound was formed in the product, and 2-methylglutaric acid was the only by-product and the content was less than 2%. In addition, many nitrilases have been developed and used in the synthesis of various pharmaceutical intermediates and fine chemicals.

Through molecular modification, the catalytic activity of nitrilase on the substrate can be improved. At present, there are many studies on improving the activity of nitrilase through molecular modification. Gong Jinsong et al. used site-directed saturation mutation to mutate the nitrilase derived from *Pseudomonas putida* CGMCC3830, and screened out three types of N40G, F50 W, and Q207E whose catalytic activity on 3-cyanopyridine was increased. Based on this, double mutant F50 W/Q207E and triple mutant N40G/F50 W/Q207E were also constructed, and their catalytic activity was twice that of the wild type. Liu Zhiqiang et al. used site-directed saturation mutation to mutate the nitrilase derived from Acidovorax *facilis*, and screened out the best mutant F168V/T201N/S192F/M191T/F192S. Compared with the wild-type nitrilase, the catalytic activity of the best mutant F168V/T201N/S192F/M191T/F192S on the substrate iminodiacetonitrile was increased by 136%.

The nitrilase cloned from *Acidovorax facilis* (*A. facilis* CCTCC NO: M 209044) has been overexpressed in *E. coli* (*Escherichia coli*) BL21 (DE3), and is capable of catalyzing 1-cyanocyclohexylacetonitrile to produce the gabapentin intermediate, 1-cyanocyclohexyl acetic acid (Catalysis Communications, 2015, 66, 121-125). Existing biocatalysts mainly exist in the form of immobilized cells and immobilized enzymes in the industrial application process. The immobilized cells and immobilized enzymes have higher requirements for the activity of the starting nitrilase cells and nitrilase proteins to compensate enzyme activity loss from immobilization. The existing nitrilase enzymes need further modification to improve the catalytic efficiency and to have higher industrial application value.

SUMMARY OF THE INVENTION

Based on the phenomenon that nitrilase derived from *Acidovorax facilis* CCTCC NO: M 209044 has sub self-assembly which is related to enzyme activity, the present invention provides a nitrilase mutant protein with increased enzyme activity, an encoding gene of the mutant protein, a recombinant vectors containing the gene, and a recombinant genetically engineering strain transformed by the recombinant vectors, and its application in the catalytic synthesis of a gabapentin intermediate, 1-cyanocyclohexyl acetic acid.

Technical solutions adopted in the present invention are as follows:

The present invention provides a nitrilase mutant, which is obtained by mutating one or two of the amino acids at position 180 and 205 of the amino acid sequence shown in SEQ ID No. 2.

Further, it is preferred that the mutant is obtained by: (1) mutating glycine at position 180 of the amino acid sequence shown in SEQ ID No. 2 into aspartic acid (G180D), and the nucleotide sequence of the encoding gene is shown in SEQ ID No. 3, and the amino acid sequence is shown in SEQ ID No. 4; (2) mutating glycine at position 180 of the amino acid sequence shown in SEQ ID No. 2 into phenylalanine (G180F), and the nucleotide sequence of the encoding gene is shown in SEQ ID No. 5, and the amino acid sequence is shown in SEQ ID No. 6; (3) mutating alanine at position 205 of the amino acid sequence shown in SEQ ID No. 2 into cysteine (A205C), and the nucleotide sequence of the encoding gene is shown in SEQ ID No. 7, and the amino acid sequence is shown in SEQ ID No. 8; or (4) mutating glycine at position 180 and alanine at position 205 of the amino acid sequence shown in SEQ ID No. 2 into aspartic acid and cysteine, respectively (G180D/A205C), and the nucleotide sequence of the encoding gene is shown in SEQ ID No. 9, and the amino acid sequence is shown in SEQ ID No. 10.

The present invention also provides an encoding gene of the nitrilase mutant, a recombinant vector constructed from the encoding gene, and recombinant genetically engineered bacteria obtained by transforming the recombinant vector into the host cell. The said vectors include but are not limited to prokaryotic expression vector pET28b, eukaryotic expression vectors (pPIC9K, pPICZa, pYD1 and pYES2/GS) and clone vectors pUC18/19 and pBluscript-SK. The said host cells include but are not limited to various conventional host cells in the field, and E. coli BL21 (DE3) is preferred in the present invention.

The present invention also provides the application of the nitrilase mutant in catalyzing 1-cyanocyclohexylacetonitrile to prepare 1-cyanocyclohexyl acetic acid, specifically, the application is carried out as follows: use wet cells, wet cell-immobilized cells or a purified nitrilase as a catalyst, 1-cyanocyclohexylacetonitrile as a substrate, and a pH4.0-10.5, 200 M phosphate buffer as a reaction medium, carry out the reaction in a constant temperature water bath at 20-60° C. and 600 rpm, after the reaction is completed, subject the reaction solution to separation and purification to obtain 1-cyanocyclohexyl acetic acid; in which, the wet wells are obtained by fermentation culture of the genetically engineered strain containing the nitrilase mutant, the purified nitrilase is obtained by subjecting the wet cells to ultrasonic breaking and then extraction. The final concentration of the substrate calculated by the volume of the reaction medium is 5-1000 mM (preferably 200 mM), the amount of the purified nitrilase calculated by the volume of the reaction system is 0.1-3 mg/mL, and the specific enzyme activity is 160~170 U/g (the wet weight of the cells); and when using the wet cells or the wet cell-immobilized cells as the catalyst, its amount calculated by the weight of the wet cells per unit volume of the buffer is 10-100 g (the weight of the wet cells)/L, preferably 50 g (the weight of the wet cells)/L.

Further, the wet cells are prepared according to the following method: the genetically engineered strain containing the nitrilase mutant is inoculated into LB medium, cultured at 37° C. for 10-12 hours, the resulting inoculum is inoculated to LB medium containing kanamycin (with the final concentration of 50 mg/L) with 1% incubating volume and cultured at 37° C.; when OD600 of the culture medium reaches 0.6-0.8, isopropyl-β-D-thiogalactopyranoside (IPTG) is added with the final concentration of 0.1 mM, and the bacteria solution is subjected to induced expression at 28° C. for 10 hours; the wet cells are harvested by centrifugation and washed with normal saline twice, thereby obtaining the wet cells.

Further, the purified nitrilase is prepared according to the following method: the wet cells of the genetically engineering strain containing the nitrilase mutant are resuspended with a pH 7.0, 100 mM $NaH_2PO_4$—$Na_2HPO_4$ buffer and ultrasonic broken (400 W, 20 min, 1 s breaking, 1 s pause), the broken product is subjected to centrifugation (8000 rpm, 15 min), and the resulting supernatant is taken as a crude enzyme solution; the crude enzyme solution is applied onto the Ni-NTA column at a flow rate of 1 mL/min which has been washed with a binding buffer, the weakly adsorbed protein impurities are eluted with an equilibrium buffer at a flow rate of 2 mL/min; then the target protein is eluted with a protein elution buffer at a flow rate of 2 mL/min and collected; finally, the obtained target protein is dialyzed with a 20 mM sodium dihydrogen phosphate-disodium hydrogen phosphate buffer as the dialysate (the MWCO of the dialysis bag is 30 KDa), and the retention is the purified nitrilase; wherein the binding buffer is a pH 8.0, 50 mM $NaH_2PO_4$ buffer containing NaCl with the final concentration of 300 mM, the equilibrium buffer is a pH 8.0, 50 mM $NaH_2PO_4$ buffer containing NaCl and imidazole with the final concentrations of 300 mM and 50 mM, the elution buffer is a pH 8.0, 50 mM $NaH_2PO_4$ buffer containing NaCl and imidazole with the final concentrations of 300 mM and 500 mM.

The catalyst of the present invention may be the recombinant expression transformant (that is, wet cells, preferably E. coli BL21 (DE3)) containing the nitrilase mutant gene, the unpurified crude nitrilase, or the purified nitrilase. If needed, it can be used after immobilization.

In the present invention, the components of the LB liquid medium and the final concentrations thereof are as follows: 10 g/L tryptone, 5 g/L yeast extract, 10 g/L sodium chloride, water as solvent, natural pH. The components of LB solid medium and the final concentrations thereof are as follows: 10 g/L tryptone, 5 g/L yeast extract, 10 g/L sodium chloride, 15 g/L agar, water as solvent, natural pH.

Compared with the prior art, advantages of the present invention are mainly embodied in: in the present invention, by semi-rational design and protein molecular modification, the specific enzyme activity of the nitrilase double mutant AcN-G180D/A205C was increased by up to 1.6 folds, and the conversion rate>99%. And the reaction time was shortened to a quarter of the original using the recombinant Escherichia coli containing the nitrilase mutant to hydrolyze 1-cyanocyclohexylacetonitrile at high temperature (50° C.). Therefore, the mutants obtained by the present invention have a good application prospect in efficiently catalyzing 1-cyanocyclohexylacetonitrile to synthesize gabapentin intermediate, 1-cyanocyclohexyl acetic acid.

SPECIFIC EMBODIMENT

The present invention is further illustrated below with specific examples, but protection scope of the present invention is not limited to these examples:

Example 1: Site-Directed Mutation and Screening

1. Selecting Mutation Sites

The present invention used site-directed mutation technology to carry out site-directed mutation at position 168 of the encoding gene of the nitrilase (GenBank Accession no.: AHW42593.1) derived from *A. facilis* CCTCC NO: M 209044 to obtain *E. coli* BL21 (DE3)/pET-28b (+)-AcN-F168V (referring to Zhang X H, et al. Activity improvement of a regioselective nitrilase from *Acidovorax facilis* and its application in the production of 1-(cyanocyclohexyl) acetic acid [J]. Process Biochemistry, 2014.). Based on this, The present invention mainly aimed at the amino acid site on "A surface" as the mutation site. After successful site-directed mutation by whole-plasmid PCR, the expression vector containing the target gene was transferred into the *Escherichia coli* host. The positive mutants were screened out by enzyme activity detection method after induced expression, and subjected to second detection to identify the mutants with increased enzyme activity, thereby obtaining mutant proteins which has self-assembly tendency and can efficiently catalyze regioselective hydrolysis of dinitrile to produce monocyanocarboxylic acid compound.

2. Single Mutation

Figure 1:
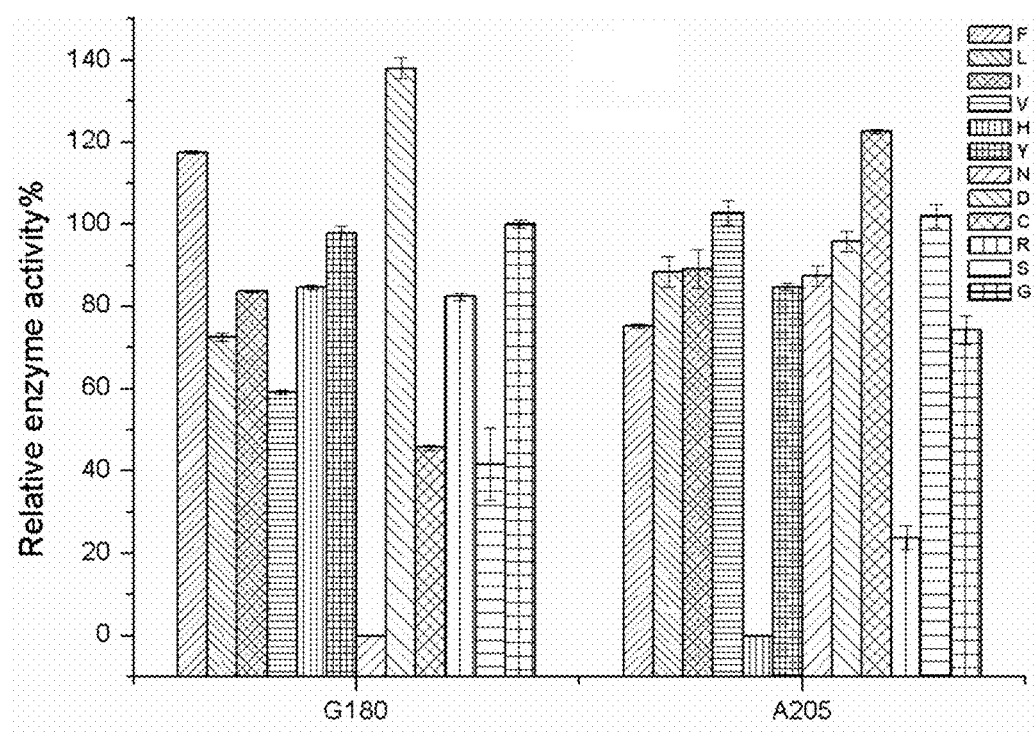
FIG. 1 is a histogram of enzyme activity of the different mutants.

The plasmid pET-28b (+)-AcN-F168V containing the nitrilase gene AcN-F168V (the nucleotide sequence shown in SEQ ID No. 1, and the amino acid sequence shown in SEQ ID No. 2) derived from *A. facilis* CCTCC NO: M 209044 was used as a template, and the site-directed mutation was carried out by whole-plasmid amplification. The PCR system (50 μL) was as follows: 0.5-20 ng of the template, 10-15 pmol of each primer (G180-f and A205-f, whose sequences is seen in in table 1), 5×PrimeSTAR Buffer (Mg2+plus), 0.2 mM dNTP, and 1.25 U PrimeSTAR HS DNA Polymerase. The PCR program was as follows: (1) pre-denaturation at 98° C. for 3 min; (2) denaturation at 98° C. for 10 s; (3) anneal at 55° C. for 5 s; (4) extension at 72° C. for 6.5 min, wherein steps (2)~(4) were cycled 30 times; and (5) finally, extension at 72° C. for 5 min, preservation at 4° C. The PCR product was identified by agarose gel electrophoresis, digested with DpnI, and then introduced into the host strain *E. coli* BL21 (DE3) which was then plated on a LB plate containing 50 μg/mL kanamycin to obtain monoclones. A total of 23 single mutants obtained by the site-directed mutation were subjected to enzyme activity test, the method of the enzyme activity test was the same as that in example 4, and the result of the enzyme activity is shown in FIG. 1. Finally, the mutation transformants *E. coli* BL21 (DE3)/pET-28b (+)-AcN-G180F (written as G180F), *E. coli* BL21 (DE3)/pET-28b (+)-AcN-G180D (written as G180D) and *E. coli* BL21 (DE3)/pET-28b (+)-AcN-A205C (written as A205C) with increased enzyme activity were screened out.

TABLE 1 primer design table

| Mutant | Sequences | Substitution |
|---|---|---|
| G180F | 5' ATGTACTCCCTGTTTGAACAGGTACAC3' (SEQ ID No: 11) | GGT to TTT |
| G180L | 5' ATGTACTCCCTGCTTGAACAGGTACAC3' (SEQ ID No: 12) | GGT to CTT |
| G180I | 5' ATGTACTCCCTGATTGAACAGGTACAC3' (SEQ ID No: 13) | GGT to ATT |
| G180V | 5' ATGTACTCCCTGGTTGAACAGGTACAC3' (SEQ ID No: 14) | GGT to GTT |
| G180Y | 5' ATGTACTCCCTGTATGAACAGGTACAC3' (SEQ ID No: 15) | GGT to TAT |
| G180H | 5' ATGTACTCCCTGCATGAACAGGTACAC3' (SEQ ID No: 16) | GGT to CAT |
| G180N | 5' ATGTACTCCCTGAATTAACAGGTACAC3' (SEQ ID No: 17) | GGT to AAT |
| G180D | 5' ATGTACTCCCTGGATGAACAGGTACAC3' (SEQ ID No: 18) | GGT to GAT |
| G180C | 5' ATGTACTCCCTGTGTGAACAGGTACAC3' (SEQ ID No: 19) | GGT to TGT |
| G180R | 5' ATGTACTCCCTGCGTGAACAGGTACAC3' (SEQ ID No: 20) | GGT to CGT |
| G180S | 5' ATGTACTCCCTGAGTGAACAGGTACAC3' (SEQ ID No: 21) | GGT to AGT |
| A205F | 5' ACCTCCATCGAGTTCAATGCGACCGTA3' (SEQ ID No: 22) | GCT to TTC |
| A205L | 5' ACCTCCATCGAGTTGAATGCGACCGTA3' (SEQ ID No: 23) | GCT to TTG |
| A205I | 5' ACCTCCATCGAGATAAATGCGACCGTA3' (SEQ ID No: 24) | GCT to ATA |
| A205V | 5' ACCTCCATCGAGGTTAATGCGACCGTA3' (SEQ ID No: 25) | GCT to GTT |
| A205Y | 5' ACCTCCATCGAGTATAATGCGACCGTA3' (SEQ ID No: 26) | GCT to TAT |
| A205H | 5' ACCTCCATCGAGCATAATGCGACCGTA3' (SEQ ID No: 27) | GCT to CAT |
| A205N | 5' ACCTCCATCGAGAATAATGCGACCGTA3' (SEQ ID No: 28) | GCT to AAT |
| A205D | 5' ACCTCCATCGAGGATAATGCGACCGTA3' (SEQ ID No: 29) | GCT to GAT |
| A205C | 5' ACCTCCATCGAGTGTAATGCGACCGTA3' (SEQ ID No: 30) | GCT to TGT |
| A205R | 5' ACCTCCATCGAGCGTAATGCGACCGTA3' (SEQ ID No: 31) | GCT to CGT |
| A205S | 5' ACCTCCATCGAGTCTAATGCGACCGTA3' (SEQ ID No: 32) | GCT to TCT |
| A205G | 5' ACCTCCATCGAGGGTAATGCGACCGTA3' (SEQ ID No: 33) | GCT to GGT |

3. Combinatorial Mutation

The plasmid pET-28b (+)-AcN-G180D containing the mutation transformant G180D (the nucleotide sequence shown in SEQ ID No. 3) was used as a template, and site-directed mutation was carried out by whole-plasmid amplification. The PCR system was the same as that in the single mutation system. The PCR product was identified by agarose gel electrophoresis, digested with DpnI, introduced into the host strain *E. coli* BL21 (DE3) and then plated on a LB plate containing 50 μg/mL kanamycin, thereby obtaining the double mutation transformant which is the combinatorial mutant *E. coli* BL21 (DE3)/pET-28b (+)-AcN-G180D/A205C (written as G180D/A205C).

Example 2: Expression of the Nitrilase Mutant

The plasmid pET-28b (+)-AcN-F168V containing the nitrilase gene AcN-F168V (shown in SEQ ID No. 1) of *Acidovorax facilis* CCTCC NO: M 209044 was constructed. The constructed expression vector pET-28b (+)-AcN-F168V was transferred into *E. coli* BL21 (DE3) for overexpression. The plasmids were subjected to site-directed saturation mutation and recombination with expression vector pET-28b (+), and then the recombinant plasmids were transformed into *E. coli* BL21 (DE3) for constructing the mutants, *E. coli* BL21 (DE3)/pET-28b (+)-AcN-G180F, *E. coli* BL21 (DE3)/pET-28b (+)-AcN-G180D, *E. coli* BL21 (DE3)/pET-28b (+)-AcN-A205C, the combinatorial mutant *E. coli* BL21 (DE3)/pET-28b (+)-AcN-G180D/A205C and the original strain *E. coli* BL21 (DE3)/pET-28b (+)-AcN-F168V (according to Zhang X H, et al. Activity improvement of a regioselective nitrilase from *Acidovorax facilis* and its application in the production of 1-(cyanocyclohexyl) acetic acid [J]. Process Biochemistry, 2014.). The obtained strains were respectively inoculated to LB medium and cultured at 37° C. for 10-12 h, the resulting inocula were respectively inoculated to LB medium containing kanamycin (with the final concentration of 50 mg/L) with 1% incubating volume, amplified and cultured at 37° C. and 150 rpm. When OD600 of the culture medium reached 0.6-0.8, isopropyl-B-D-thiogalactopyranoside (IPTG) was added with the final concentration of 0.1 mM to carry out induced expression at 28° C. for 10 hours. The wet cells were harvested by centrifugation and washed with normal saline twice. The immobilized cells were obtained by subjecting the wet cells to immobilization (according to the immobilization method in CN107177576A), and the purified nitrilase was obtained by subjecting the wet cells to ultrasonic breaking and then purification (according to the purification process in example 3).

Example 3: Purification of the Nitrilase and its Mutants (1) Binding buffer (50 mM $NaH_2PO_4$, 300 mM NaCl, pH 8.0) was added to the wet cells obtained in example 2, the cells were resuspended, ultrasonic broken (400 W, 20 min, 1 s breaking, 1 s pause) and centrifuged (8000 rpm, 15 min). The supernatant was a crude enzyme solution for separation and purification.

(2) After pre-filling a 10 mL Ni-NTA affinity column, a binding buffer (50 mM $NaH_2PO_4$, 300 mM NaCl, pH 8.0) was used to wash the column at a flow rate of 2 mL/min.

(3) After the Ni-NTA column was washed with 8-10 column volume, the obtained crude enzyme solution was applied onto the Ni-NTA column at a flow rate of 1 mL/min, and the target protein bound to the column. After loading, a large amount of unbound protein impurities which did not bind to the resin would be directly removed.

(4) The weakly adsorbed protein impurities were eluted with an equilibrium buffer (50 mM $NaH_2PO_4$, 300 mM NaCl, 50 mM imidazole, pH 8.0) at a flow rate of 2 mL/min.

(5) The target protein was eluted with a protein elution buffer (50 mM $NaH_2PO_4$, 300 mM NaCl, 500 mM imidazole, pH 8.0) at a flow rate of 2 mL/min and collected.

(6) The collected target protein was dialyzed (the MWCO of the dialysis bag is 30 KDa) with a 20 mM sodium dihydrogen phosphate-disodium hydrogen phosphate buffer as the dialysate, and the retention was the purified nitrilase.

Figure 2:
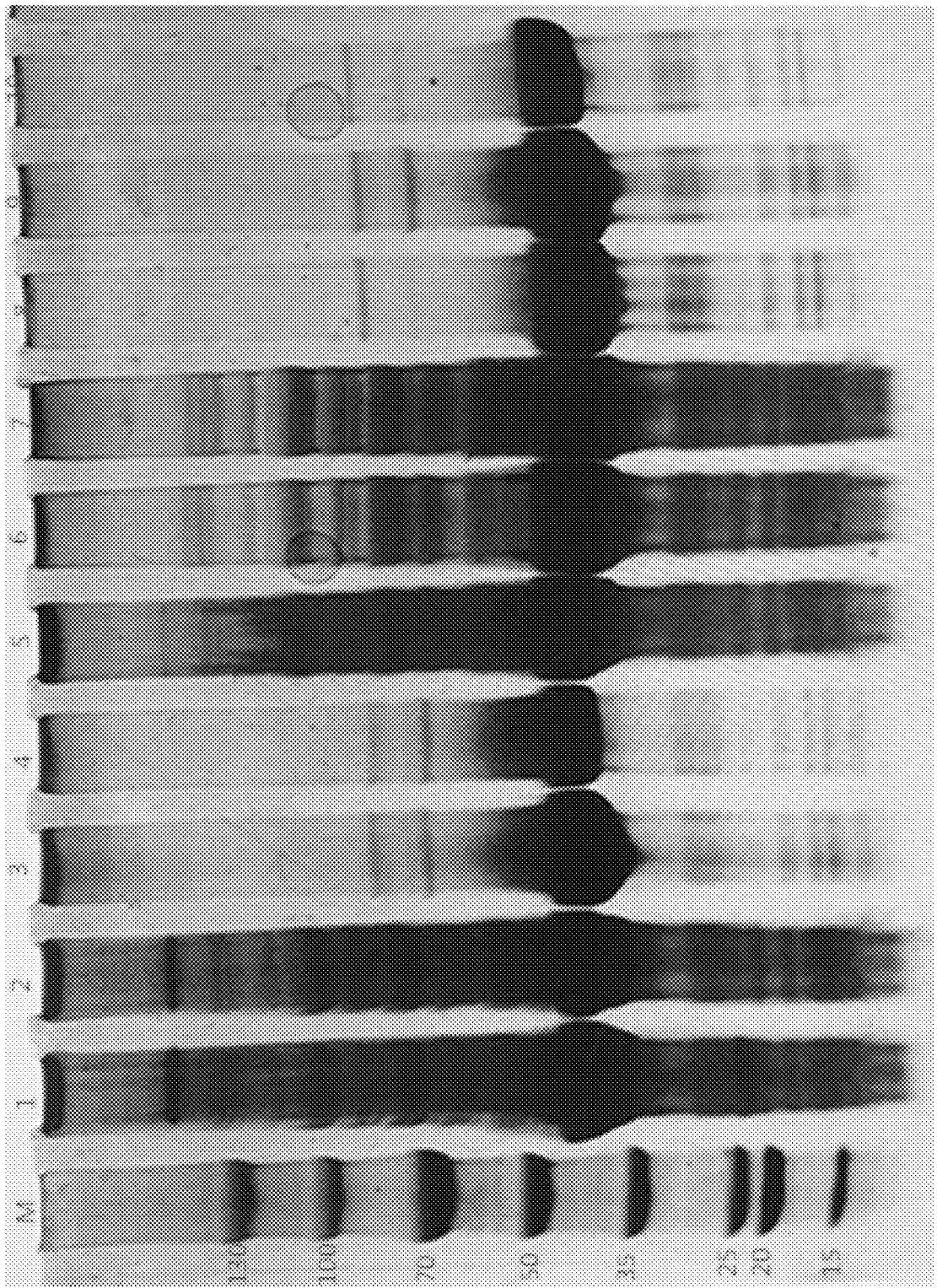
FIG. 2 is an SDS-PAGE of the nitrilase E. coli BL21 (DE3)/pET-28b (+)-AcN and its mutant transformants E. coli BL21 (DE3)/pET-28b (+)-AcN-G180D, E. coli BL21 (DE3)/pET-28b (+)-AcN-G180F, E. coli BL21 (DE3)/pET-28b (+)-AcN-A205C and the double mutant E. coli BL21 (DE3)/pET-28b (+)-SDS-PAGE of AcN-G180D/A205C, wherein lane 1 is AcN crude enzyme solution, lane 2 is G180D/A205C crude enzyme solution, lane 3 is AcN purified enzyme solution, lane 4 is G180D/A205C purified enzyme solution, lane 5 It is G180D crude enzyme solution, lane 6 is G180F crude enzyme solution, lane 7 is A205C crude enzyme solution, lane 8 is G180D purified enzyme solution, lane 9 is G180F purified enzyme solution, and lane 10 is A205C purified enzyme solution.

(7) The purified proteins were analyzed by SDS-PAGE, and the results of protein electrophoresis are shown in FIG. 2.

Example 4 Activity Determination of the Nitrilases

Figure 3:
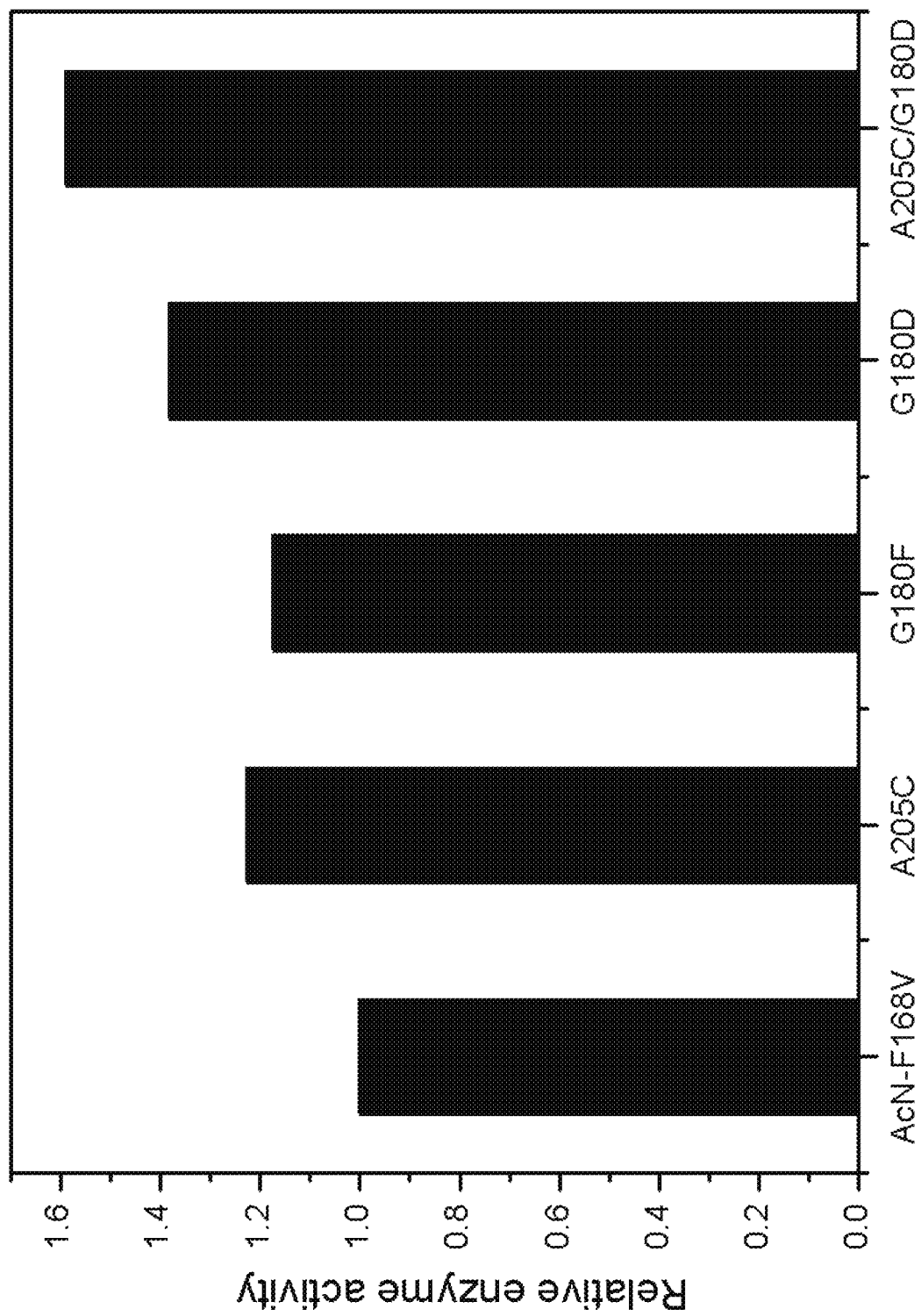
FIG. 3 is a comparison curve diagram of enzyme activity of the nitrilase and its mutants.

The activity of the purified nitrilases from example 3 was determined. A reaction system (10 mL) for nitrilase activity assay was as follows: a 100 mM, pH 7.0 sodium dihydrogen phosphate-disodium hydrogen phosphate buffer, 200 mM 1-cyanocyclohexylacetonitrile, and 30 mg of the purified nitrilase. The reaction solution was preheated at 45° C. for 10 min and then reacted at 150 rpm for 10 min. 500 μL of the supernatant was sampled, and 500 μL of 2 M HCl was added to terminate the reaction, and the conversion rate of 1-cyanocyclohexyl acetic acid was determined by liquid chromatography (Agilent) external standard method. The column was J&K Scientific C18-H column (4.6×250 mm, 5 μm, 120 Å), and the mobile phase was a buffer (0.58 g/L diammonium phosphate, 1.8375 g/L sodium perchlorate, pH was adjusted to 1.8 by perchloric acid, the solvent is deionized water and acetonitrile in a ratio of 76:24 (v/v), the flow rate was 1 mL/min, the ultraviolet detection wavelength was 215 nm, and the column temperature was 40° C. The results of relative enzyme activity of each mutant are shown in FIG. 3.

Enzyme activity definition (U): the amount of enzyme required to catalyze the formation of 1 μmol of 1-cyanocyclohexyl acetic acid per minute at 45° C., in a pH 7.0, 100 mM sodium dihydrogen phosphate-disodium hydrogen phosphate buffer was defined as 1 U.

Example 5: Determination of Kinetic Parameters of the Nitrilase and its Mutants The kinetic parameters of the purified protein in example 3 were determined, using 1-cyanocyclohexylacetonitrile as the substrate and the pure enzyme solutions of AcN-F168V, G180D, A205C, G180F, and G180D/A205C as the catalyst.

10 mL of the reaction system was as follows: the purified enzyme solution (165 U/g) was diluted 10 times with a pH 7.0, 20 mM phosphate buffer and the final concentration of the purified nitrilase was 0.2 mg/mL. The resulting enzyme solution was put into a reaction container, added with the substrate at final concentrations of 6.75-40.49 mM (6.75, 13.50, 20.24, 26.99, 33.74 and 40.49 mM, respectively) and added with a pH 7.0, 20 mM phosphate buffer as the reaction medium up to 10 mL, the reaction solution was reacted at 45° C. and 600 rpm for 5 min, 500 μL of the sample was taken out, 500 μL of 2 M HCl was added to terminate the reaction, and the concentration of 1-cyanocyclohexyl acetic acid in the reaction solution was determined by HPLC (The detection and analysis conditions are the same as that in example 4).

Collected test data was used to conduct nonlinear fitting by Origin, thereby obtaining the $K_m$ value and $K_{cat}$ value of the nitrilase *E. coli* BL21 (DE3)/pET-28b (+)-AcN-F168V and its combinatorial mutants *E. coli* BL21 (DE3)/pET-28b (+)-AcN-G180D, *E. coli* BL21 (DE3)/pET-28b (+)-AcN-G180F, *E. coli* BL21 (DE3)/pET-28b (+)-AcN-A205C and *E. coli* BL21 (DE3)/pET-28b (+)-AcN-G180D/A205C as shown in table 2. It can be found that the $K_{cat}$ of the double mutants is significantly improved compared with that of AcN, which indicates that the activity of the modified nitrilase is indeed increased, and their $K_m$ reflects a slight decrease in the affinity of the modified enzyme to the substrate.

TABLE 2

| Kinetic parameters of the nitrilase mutants | | | | |
|---|---|---|---|---|
| Enzyme | $K_m$[mM] | $V_{max}$[mmolmg$^{-1}$min$^{-1}$] | $K_{cat}$[s$^{-1}$] | $K_{cat}/K_m$[mM$^{-1}$h$^{-1}$] |
| AcN-F168V | 16.25 ± 5.37 | 1.53 ± 0.19 | 5573s$^{-1}$ | 342.95 |
| G180D | 3.21 ± 1.41 | 1.98 ± 0.13 | 6624s$^{-1}$ | 2063.55 |
| G180F | 5.88 ± 1.58 | 2.35 ± 0.14 | 7612s$^{-1}$ | 1294.56 |
| A205C | 3.40 ± 0.78 | 1.63 ± 0.059 | 8317s$^{-1}$ | 2446.18 |
| G180D/A205C | 19.65 ± 7.40 | 4.78 ± 0.73 | 24139s$^{-1}$ | 1228.45 |

Example 6: Determination of Optimal Temperature of Nitrilase and its Mutants The optimal temperature of the purified protein in example 3 were determined, using 1-cyanocyclohexylacetonitrile as the substrate and the pure enzyme solution of nitrilase AcN-F168V (whose specific enzyme activity was 104 U/g calculated by the weight of the wet cells) or the nitrilase combinatorial mutant G180D/A205C (whose specific enzyme activity was 165 U/g calculated by the weight of the wet cells) as the catalyst.

Figure 4:
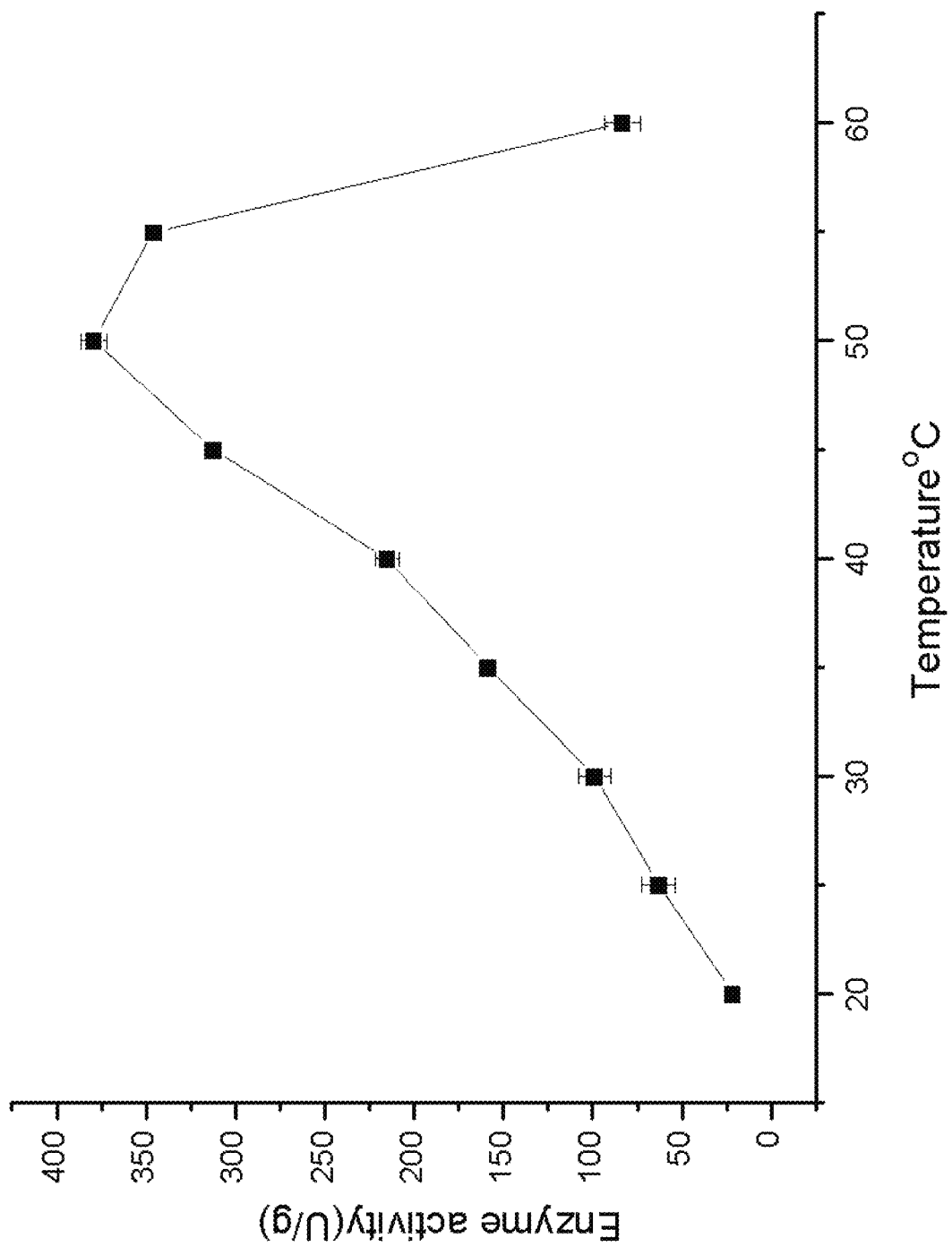
FIG. 4 is a curve diagram of the optimal temperature of the nitrilase double mutant E. coli BL21 (DE3)/pET-28b (+)-AcN-G180D/A205C.

10 mL of the reaction system was as follows: the collected purified nitrilase (165 U/g) was diluted 10 times with a pH 7.0, 20 mM phosphate buffer and the final concentration of the purified nitrilase was 0.2 mg/mL. The resulting enzyme solution was put into a reaction container, added with the substrate at a final concentration of 200 mM and added with a pH 7.0, 20 mM phosphate buffer as the reaction medium up to 10 mL, the reaction solution was reacted at 600 rpm for 10 min, the reaction temperature is 20-60° C. (20, 25, 30, 35, 40, 45, 50, 55 and 60° C., respectively), 500 μL of the sample was taken out, 500 μL of 2 M HCl was added to terminate the reaction, and the concentration of 1-cyanocyclohexyl acetic acid in the reaction solution was determined by HPLC. The results are shown in FIG. 4, and the optimal temperature of the double mutant is 50° C. Under the same conditions, the optimal temperature of the nitrilase AcN-F168V is 50° C.

Example 7: Determination of the Optimal pH of the Nitrilase and its Mutants

The optimal temperature of the purified protein in example 3 were determined, using 1-cyanocyclohexylacetonitrile as the substrate and the pure enzyme solution of nitrilase AcN-F168V (whose specific enzyme activity was 104 U/g calculated by the weight of the wet cells) or the nitrilase combinatorial mutant G180D/A205C (whose specific enzyme activity was 165 U/g calculated by the weight of the wet cells) as the catalyst.

Figure 5:
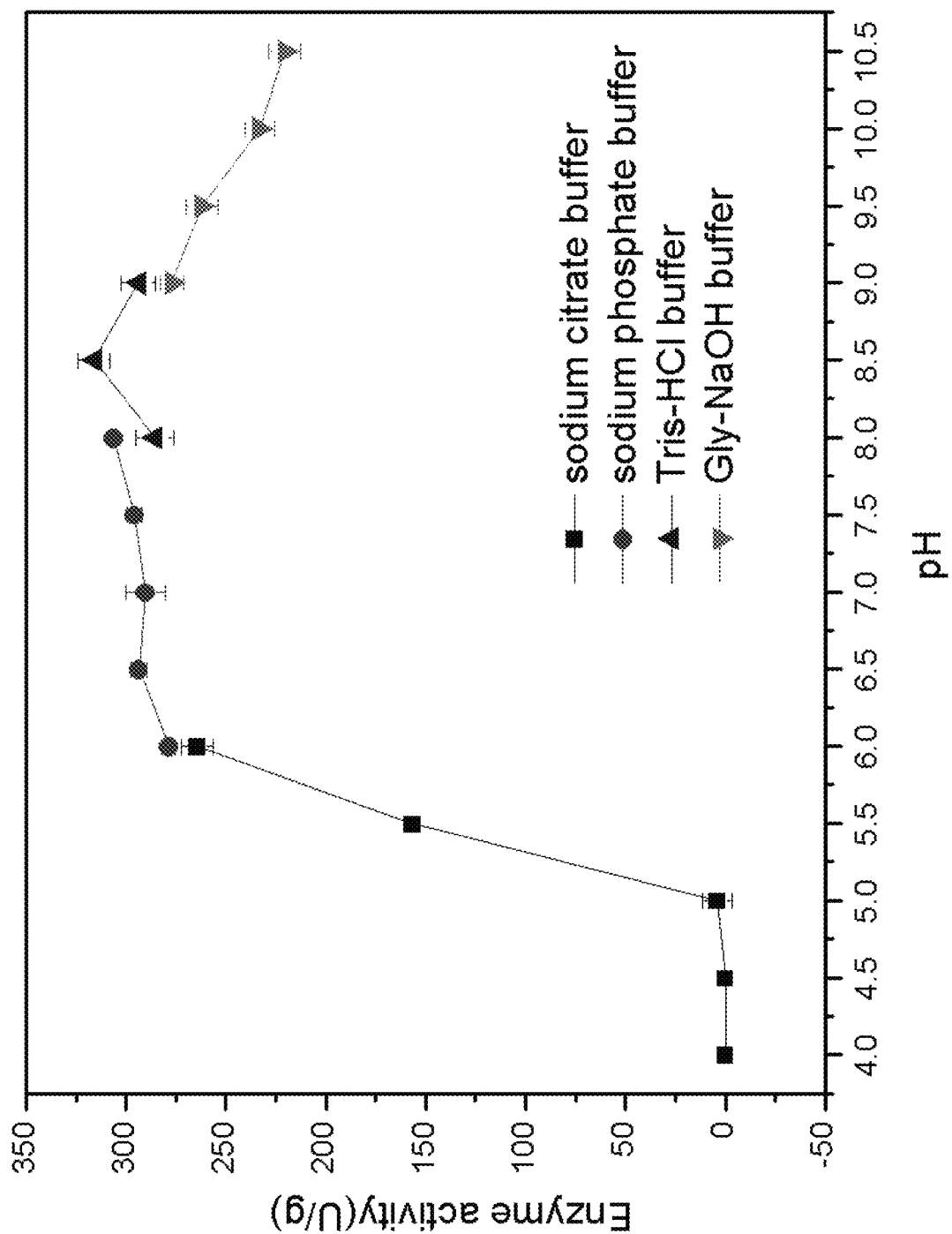
FIG. 5 is a curve diagram of the optimal pH of the nitrilase double mutant E. coli BL21 (DE3)/pET-28b (+)-AcN-G180D/A205C.

10 mL of the reaction system was as follows: the purified enzyme solution of G180D/A205C (165 U/g) was diluted 10 times with a pH 7.0, 20 mM phosphate buffer and the final concentration of the purified nitrilase was 0.2 mg/mL. The resulting enzyme solution was put into a reaction container, added with the substrate at a final concentration of 200 mM and added with a 100 mM phosphate buffer as the reaction medium up to 10 mL, and the pH of the phosphate buffer was 4, 4.5, 5, 5.5, 6, 6.5, 7, 7.5, 8, 8.5, 9, 9.5, 10 and 10.5, respectively. The reaction solution was reacted at 45° C. and 600 rpm for 10 min, 500 μL of the sample was taken out, 500 μL of 2 M HCl was added to terminate the reaction, and the concentration of 1-cyanocyclohexyl acetic acid in the reaction solution was determined by HPLC. The results are shown in FIG. 5, and the optimal pH of the double mutant is 8.5. Under the same conditions, the optimal pH of the nitrilase AcN-F168V is 7.

Example 8: Converting 200 mM Cyanocyclohexylacetonitrile by the Nitrilase and its Mutants The reaction process of the purified nitrilase and its mutants in example 3 were determined, using 1-cyanocyclohexylacetonitrile as the substrate and the pure enzyme solution of the nitrilase AcN-F168V (whose specific enzyme activity was 104 U/g calculated by the weight of the wet cells) or the nitrilase combinatorial mutant G180D/A205C (whose specific enzyme activity was 165 U/g calculated by the weight of the wet cells) as the catalyst.

Figure 6:
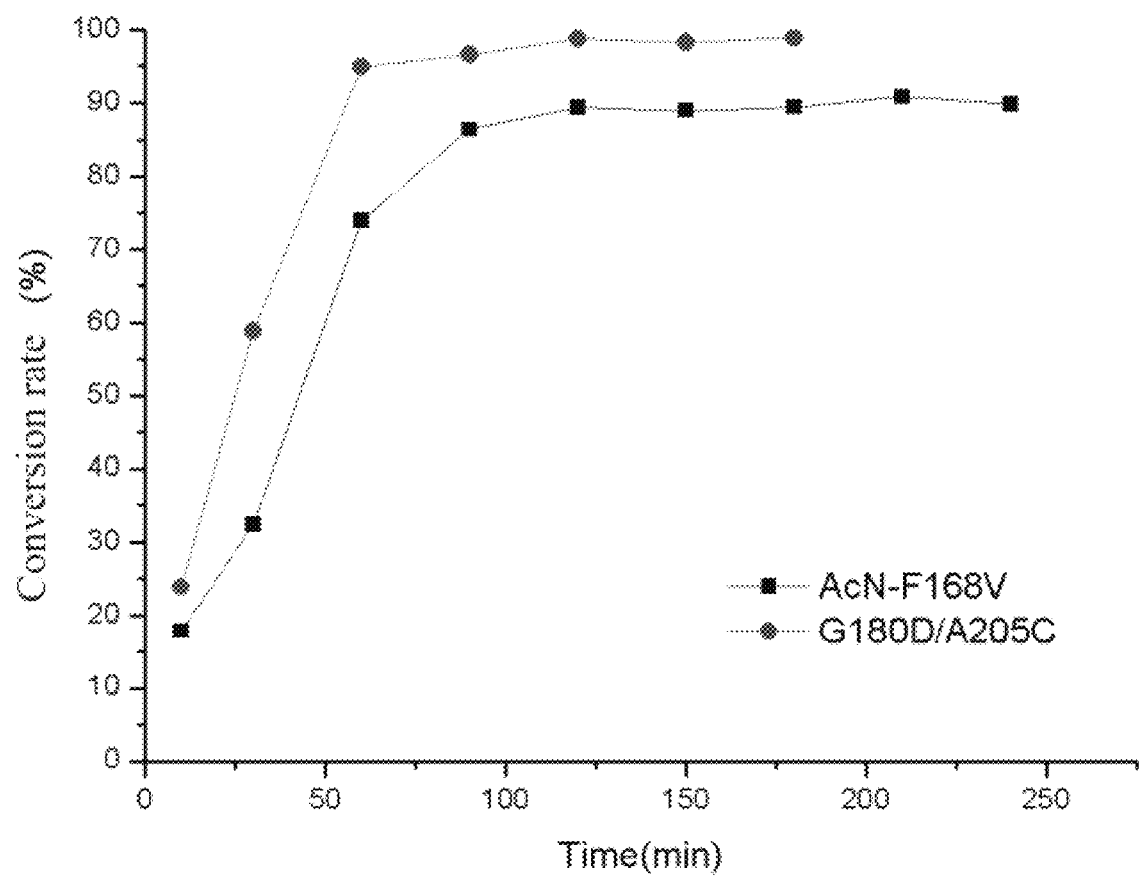
FIG. 6 is the reaction process of nitrilase AcN-F168V and its double mutant.

10 mL of the reaction system was as follows: the collected purified enzyme solution was diluted 10 times with a pH 7.0, 20 mM phosphate buffer and the final concentration of the purified nitrilase was 0.2 mg/mL. The resulting enzyme solution was put into a reaction container, added with the substrate at a final concentration of 200 mM, and added with a pH 7.0, 20 mM phosphate buffer as the reaction medium up to 10 mL, the reaction solution was reacted at 45° C. and 600 rpm, 500 μL of the sample was taken out at different time, 500 μL of 2 M HCl was added to terminate the reaction, and the concentration of 1-cyanocyclohexyl acetic acid in the reaction solution was determined by HPLC. The reaction process of the nitrilase AcN-F168V and its mutant is shown in FIG. 6, and the conversion rate was over 99%. As shown in FIG. 6, the double mutant G180D/A205C could completely hydrolyze the substrate within 60 min, which is shorter than the nitrilase AcN-F168V.

The invention claimed is:

1. A nitrilase mutant, wherein the mutant has nitrilase activity of catalyzing the conversion of the substrate dinitrile to a product of monocyano carboxylic acid compound, and the nitrilase mutant comprises the amino acid sequence of SEQ ID NO: 2, except for the substitution G180D, the substitution G180F, the substitution A205C, or the substitutions G180D and A205C.

2. A polynucleotide comprising a nucleotide sequence encoding the nitrilase mutant of claim 1.

3. A recombinant genetically engineered E. coli host cell transformed with the polynucleotide of claim 2.

4. A method for producing 1-cyanocyclohexyl acetic acid, the method comprising:
reacting a catalyst and a substrate in a reaction medium to produce a reaction solution comprising 1-cyanocyclohexyl acetic acid,
wherein the catalyst is wet cells comprising the nitrilase mutant of claim 2,
wherein the wet cells are obtained by fermentation culture of a genetically engineered E. coli cell expressing the nitrilase mutant, immobilized E. coli cells comprising the nitrilase mutant or the nitrilase mutant,
wherein the nitrilase mutant is purified,
wherein the purified nitrilase is obtained by subjecting the wet cells to ultrasonic breaking and centrifugation,
wherein the substrate is 1-cyanocyclohexylacetonitrile,
wherein the reaction medium is a pH 7.0, 200 mM disodium hydrogen phosphate-sodium dihyrdrogen phosphate buffer,
wherein the reaction is carried out in a constant temperature water bath at 25-50° C., and
wherein, after the reaction is completed, the reaction solution is subjected to separation and purification to obtain the 1-cyanocyclohexyl acetic acid.

5. The method of claim 4, wherein the final concentration of the substrate in the reaction medium is 5-1000 mM, and wherein catalyst is wet cells and the concentration of the wet cells in the reaction medium is 10-100 g/L.

6. The method of claim 4, wherein the wet cells are prepared according to the following method:
culturing an LB medium with the genetically engineered E. coli host expressing the nitrilase mutant at 37° C. for 10-12 hours to produce an inoculum;
inoculating the LB medium with the inoculum with a 1% incubating volume, wherein the LM medium contains 50 mg/L kanamycin and culturing at 37° C.;
inducing an expression of the nitrilase mutant by adding isopropyl-p-D-thiogalactopyranoside to a final concentration of 0.1 mM when the $OD_{600}$ of the culture reaches 0.6-0.8 and culturing at 28° C. for 10 hours;
harvesting cells by centrifugation; and
washing the cells with normal saline twice, thereby obtaining the wet cells.

7. The method of claim 4, wherein the purified nitrilase is prepared according to the following method:
resuspending the wet cells with a pH 7.0, 100 mM $NaH_2PO_4$—$Na_2HPO_4$ buffer containing 300 mM NaCl;
ultrasonically breaking the resuspended wet cells under the conditions of 400 W, 25 min, 1 s breaking and 1 s pause;
centrifuging the broken cells at 8000 rpm for 15 min to obtain a supernatant, wherein the supernatant is a crude enzyme solution;
applying the crude enzyme solution to a Ni-NTA column that has been washed with an equilibrium buffer, wherein the equilibrium buffer is a pH 8.0, 50 mM $NaH_2PO_4$ buffer containing 300 mM NaCl, and 50 mM imidazole, pH 8.0;
applying a first elution buffer to the Ni-NTA column with the applied crude enzyme solution at a flow rate of 2 mL/min to elute weakly absorbed protein impurities, wherein the first elution buffer is pH 8.0, 50 mM $NaH_2PO_4$ buffer containing 300 mM NaCl, and 50 mM imidazole;
applying a second elution buffer to the Ni-NTA column with the first elution buffer at a flow rate of 2 mL/min to elute and collect the nitrilase mutant, wherein the second elution buffer is pH 8.0, 50 mM NaH$_2$PO$_4$ buffer containing 300 mM NaCl, and 50 mM imidazole; and dialyzing the collected nitrilase mutant with with a 20 mM sodium dihydrogen phosphate-disodium hydrogen phosphate buffer.

\* \* \* \* \*

SEQUENCE LISTING

<160> NUMBER OF SEQ ID NOS: 33

<210> SEQ ID NO 1
<211> LENGTH: 1116
<212> TYPE: DNA
<213> ORGANISM: Acidovorax facilis

<400> SEQUENCE: 1

```
atggtatctt caactccaa atttctggct gctaccgtac aggctgaacc ggtttggctg      60
gacgcggacg caactatcga taaatctatt ggtatcatcg aggaggcggc ccagaaaggt     120
gcgtctctga ttgccttccc ggaagttttc atccctggtt acccgtattg ggcctggctg    180
ggtgacgtaa agtactccct gtccttcacc tcccgttacc acgaaaactc cctggaactg    240
ggtgacgacc gtatgcgccg tctgcaactg gctgcgcgtc gtaacaaaat cgcgctggtt    300
atgggttaca gcgagcgtga ggcaggcagc cgctacctgt cccaggtctt tatcgacgaa    360
cgtggtgaaa tcgttgctaa ccgtcgtaaa ctgaaaccaa ctcacgttga acgtacgatt    420
tatggtgaag caacggtac cgactttctg acgcatgact tcgcatttgg tcgtgttggt     480
ggtctgaact gctgggagca cgttcagccg ctgtccaaat tcatgatgta ctccctgggt    540
gaacaggtac acgtcgcttc ttggccggct atgtccccgc tgcaaccgga cgtgtttcaa    600
acctccatcg aggctaatgc gaccgtaacc cgctcctatg ctattgaagg ccaaaccttc    660
gttctgtgct ctacgcaggt tatcggtccg tctgcaattg aaaccttctg tctgaacgat    720
gagcaacgtg cactgctgcc gcagggttgc ggttgggcgc gtatctacgg cccggacggc    780
agcgaactgg ccaagccgct ggctgaagac gcagagggta ttctgtacgc agaaatcgat    840
ctggaacaga ttctgctggc caaggctggc gctgatccgg ttggtcacta cagccgccct    900
gatgtcctgt ccgtgcagtt cgaccccgcgt aaccacaccc cggtacaccg cattggtatc   960
gatggccgtc tggatgttaa cacgcgttcc cgtgtagaaa actttcgcct gcgtcaggca   1020
gcagaacagg aacgtcaggc cagcaaacgt ctgggcacga aactgtttga acagtctctg  1080
ctggcggagg agccggtacc agccaaactc gagatt                             1116
```

<210> SEQ ID NO 2
<211> LENGTH: 372
<212> TYPE: PRT
<213> ORGANISM: Acidovorax facilis

<400> SEQUENCE: 2

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Thr Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Pro Val Pro Ala
        355                 360                 365

Lys Leu Glu Ile
    370

<210> SEQ ID NO 3
<211> LENGTH: 1116
<212> TYPE: DNA
<213> ORGANISM: Acidovorax facilis

<400> SEQUENCE: 3

```
atggtatctt acaactccaa atttctggct gctaccgtac aggctgaacc ggtttggctg      60
gacgcggacg caactatcga taaatctatt ggtatcatcg aggaggcggc ccagaaaggt     120
gcgtctctga ttgccttccc ggaagttttc atccctggtt accgtattgg gcctggctg      180 ggtgacgtaa agtactccct gtccttcacc tcccgttacc acgaaaactc cctggaactg     240
ggtgacgacc gtatgcgccg tctgcaactg gctgcgcgtc gtaacaaaat cgcgctggtt     300
atgggttaca gcgagcgtga ggcaggcagc cgctacctgt cccaggtctt tatcgacgaa     360
cgtggtgaaa tcgttgctaa ccgtcgtaaa ctgaaaccaa ctcacgttga cgtacgatt      420 tatggtgaag caacggtac cgactttctg acgcatgact cgcatttgg tcgtgttggt       480 ggtctgaact gctgggagca cgttcagccg ctgtccaaat tcatgatgta ctccctggat     540
gaacaggtac acgtcgcttc ttggccggct atgtccccgc tgcaaccgga cgtgtttcaa     600
acctccatcg aggctaatgc gaccgtaacc cgctcctatg ctattgaagg ccaaaccttc     660
gttctgtgct ctacgcaggt tatcggtccg tctgcaattg aaaccttctg tctgaacgat     720
gagcaacgtg cactgctgcc gcagggttgc ggttgggcgc gtatctacgg cccggacggc     780
agcgaactgg ccaagccgct ggctgaagac gcagagggta ttctgtacgc agaaatcgat     840
ctggaacaga ttctgctggc caaggctggc gctgatccgg ttggtcacta cagccgccct     900
gatgtcctgt ccgtgcagtt cgaccgcgt aaccacaccc cggtacaccg cattggtatc     960
```
gatggccgtc tggatgttaa cacgcgttcc cgtgtagaaa actttcgcct gcgtcaggca 1020
gcagaacagg aacgtcaggc cagcaaacgt ctgggcacga aactgtttga acagtctctg 1080
ctggcggagg agccggtacc agccaaactc gagatt 1116

<210> SEQ ID NO 4
<211> LENGTH: 372
<212> TYPE: PRT
<213> ORGANISM: Acidovorax facilis

<400> SEQUENCE: 4

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Asp Glu Gln Val His Val Ala Ser Trp Pro Ala Met Ser
            180                 185                 190

Pro Leu Gln Pro Asp Val Phe Gln Thr Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys Leu Glu Ile
    370

<210> SEQ ID NO 5
<211> LENGTH: 1116
<212> TYPE: DNA
<213> ORGANISM: Acidovorax facilis

<400> SEQUENCE: 5

```
atggtatctt acaactccaa atttctggct gctaccgtac aggctgaacc ggtttggctg      60
gacgcggacg caactatcga taatctatt ggtatcatcg aggaggcggc ccagaaaggt     120
gcgtctctga ttgccttccc ggaagttttc atccctggtt accgtattg ggcctggctg     180
ggtgacgtaa agtactccct gtccttcacc tcccgttacc acgaaaactc cctggaactg     240
ggtgacgacc gtatgcgccg tctgcaactg gctgcgcgtc gtaacaaaat cgcgctggtt     300
atgggttaca gcgagcgtga ggcaggcagc cgctacctgt cccaggtctt tatcgacgaa     360
cgtggtgaaa tcgttgctaa ccgtcgtaaa ctgaaaccaa ctcacgttga acgtacgatt     420
tatggtgaag caacggtac cgactttctg acgcatgact cgcatttgg tcgtgttggt     480
ggtctgaact gctgggagca cgttcagccg ctgtccaaat tcatgatgta ctccctgttt     540
gaacaggtac acgtcgcttc ttggccggct atgtccccgc tgcaaccgga cgtgtttcaa     600
acctccatcg aggctaatgc gaccgtaacc cgctcctatg ctattgaagg ccaaaccttc     660
gttctgtgct ctacgcaggt tatcggtccg tctgcaattg aaaccttctg tctgaacgat     720
gagcaacgtg cactgctgcc gcagggttgc ggttgggcgc gtatctacgg cccggacggc     780
agcgaactgg ccaagccgct ggctgaagac gcagagggta ttctgtacgc agaaatcgat     840
ctggaacaga ttctgctggc caaggctggc gctgatccgg ttggtcacta cagccgccct     900
gatgtcctgt ccgtgcagtt cgacccgcgt aaccacaccc cggtacaccg cattggtatc     960
gatggccgtc tggatgttaa cacgcgttcc cgtgtagaaa actttcgcct gcgtcaggca    1020
gcagaacagg aacgtcaggc cagcaaacgt ctgggcacga aactgtttga acagtctctg    1080
ctggcggagg agccggtacc agccaaactc gagatt                              1116
```

<210> SEQ ID NO 6
<211> LENGTH: 372
<212> TYPE: PRT
<213> ORGANISM: Acidovorax facilis

<400> SEQUENCE: 6

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

```
Ile Ala Leu Val Met Gly Tyr Ser Glu Arg Glu Ala Gly Ser Arg Tyr
                100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Phe Glu Gln Val His Val Ala Ser Trp Pro Ala Met Ser
            180                 185                 190

Pro Leu Gln Pro Asp Val Phe Gln Thr Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys Leu Glu Ile
        370

<210> SEQ ID NO 7
<211> LENGTH: 1116
<212> TYPE: DNA
<213> ORGANISM: Acidovorax facilis

<400> SEQUENCE: 7
atggtatctt acaactccaa atttctggct gctaccgtac aggctgaacc ggtttggctg      60
gacgcggacg caactatcga taaatctatt ggtatcatcg aggaggcggc ccagaaaggt     120
gcgtctctga ttgccttccc ggaagttttc atccctggat accgtattg ggcctggctg     180 ggtgacgtaa agtactccct gtccttcacc tcccgttacc acgaaaactc cctggaactg     240
ggtgacgacc gtatgcgccg tctgcaactg gctgcgcgtc gtaacaaaat cgcgctggtt     300
atgggttaca gcgagcgtga ggcaggcagc cgctacctgt cccaggtctt tatcgacgaa     360
cgtggtgaaa tcgttgctaa ccgtcgtaaa ctgaaaccaa ctcacgttga acgtacgatt     420
tatggtgaag caacggtac cgactttctg acgcatgact cgcatttgg tcgtgttggt     480 ggtctgaact gctgggagca cgttcagccg ctgtccaaat tcatgatgta ctccctgggt     540
```

```
gaacaggtac acgtcgcttc ttggccggct atgtccccgc tgcaaccgga cgtgtttcaa    600
acctccatcg agtgtaatgc gaccgtaacc cgctcctatg ctattgaagg ccaaaccttc    660
gttctgtgct ctacgcaggt tatcggtccg tctgcaattg aaaccttctg tctgaacgat    720
gagcaacgtg cactgctgcc gcagggttgc ggttgggcgc gtatctacgg cccggacggc    780
agcgaactgg ccaagccgct ggctgaagac gcagagggta ttctgtacgc agaaatcgat    840
ctggaacaga ttctgctggc caaggctggc gctgatccgg ttggtcacta cagccgccct    900
gatgtcctgt ccgtgcagtt cgacccgcgt aaccacaccc cggtacaccg cattggtatc    960
gatggccgtc tggatgttaa cacgcgttcc cgtgtagaaa actttcgcct gcgtcaggca   1020
gcagaacagg aacgtcaggc cagcaaacgt ctgggcacga aactgtttga acagtctctg   1080
ctggcggagg agccggtacc agccaaactc gagatt                             1116
```

<210> SEQ ID NO 8
<211> LENGTH: 372
<212> TYPE: PRT
<213> ORGANISM: Acidovorax facilis

<400> SEQUENCE: 8

```
Met Val Ser Tyr Asn Ser Lys Phe Leu Ala Ala Thr Val Gln Ala Glu
  1               5                  10                  15

Pro Val Trp Leu Asp Ala Asp Ala Thr Ile Asp Lys Ser Ile Gly Ile
             20                  25                  30

Ile Glu Glu Ala Ala Gln Lys Gly Ala Ser Leu Ile Ala Phe Pro Glu
         35                  40                  45

Val Phe Ile Pro Gly Tyr Pro Tyr Trp Ala Trp Leu Gly Asp Val Lys
     50                  55                  60

Tyr Ser Leu Ser Phe Thr Ser Arg Tyr His Glu Asn Ser Leu Glu Leu
 65                  70                  75                  80

Gly Asp Asp Arg Met Arg Arg Leu Gln Leu Ala Ala Arg Arg Asn Lys
                 85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Thr Ser Ile Glu Cys Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270
```

Gly Ile Leu Tyr Ala Glu Ile Asp Leu Glu Gln Ile Leu Ala Lys
            275                 280                 285

Ala Gly Ala Asp Pro Val Gly His Tyr Ser Arg Pro Asp Val Leu Ser
        290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
            325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Pro Val Pro Ala
            355                 360                 365

Lys Leu Glu Ile
    370

<210> SEQ ID NO 9
<211> LENGTH: 1116
<212> TYPE: DNA
<213> ORGANISM: Acidovorax facilis

<400> SEQUENCE: 9
atggtatctt acaactccaa atttctggct gctaccgtac aggctgaacc ggtttggctg      60
gacgcggacg caactatcga taaatctatt ggtatcatcg aggaggcggc ccagaaaggt     120
gcgtctctga ttgccttccc ggaagttttc atccctggat acccgtattg ggcctggctg     180
ggtgacgtaa agtactccct gtccttcacc tcccgttacc acgaaaactc cctggaactg     240
ggtgacgacc gtatgcgccg tctgcaactg gctgcgcgtc gtaacaaaat cgcgctggtt     300
atgggttaca gcgagcgtga ggcaggcagc cgctacctgt cccaggtctt tatcgacgaa     360
cgtggtgaaa tcgttgctaa ccgtcgtaaa ctgaaaccaa ctcacgttga acgtacgatt     420
tatggtgaag caacggtac cgactttctg acgcatgact cgcatttggt cgtgttggt       480
ggtctgaact gctgggagca cgttcagccg ctgtccaaat tcatgatgta ctccctggtt     540
gaacaggtac acgtcgcttc ttggccggct atgtccccgc tgcaaccgga cgtgtttcaa     600
acctccatcg agtgtaatgc gaccgtaacc cgctcctatg ctattgaagg ccaaaccttc     660
gttctgtgct ctacgcaggt tatcggtccg tctgcaattg aaaccttctg tctgaacgat     720
gagcaacgtg cactgctgcc gcagggttgc ggttgggcgc gtatctacgg cccggacggc     780
agcgaactgg ccaagccgct ggctgaagac gcagagggta ttctgtacgc agaaatcgat     840
ctggaacaga ttctgctggc caaggctggc gctgatccgg ttggtcacta cagccgccct     900
gatgtcctgt ccgtgcagtt cgacccgcgt aaccacaccc cggtacaccg cattggtatc     960
gatggccgtc tggatgttaa cacgcgttcc cgtgtagaaa actttcgcct gcgtcaggca    1020
gcagaacagg aacgtcaggc cagcaaacgt ctgggcacga aactgtttga acagtctctg    1080
ctggcggagg agccggtacc agccaaactc gagatt                              1116

<210> SEQ ID NO 10
<211> LENGTH: 372
<212> TYPE: PRT
<213> ORGANISM: Acidovorax facilis

<400> SEQUENCE: 10

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
               20                  25                  30

Ile Glu Glu Ala Ala Gln Lys Gly Ala Ser Leu Ile Ala Phe Pro Glu
            35                  40                  45

Val Phe Ile Pro Gly Tyr Pro Tyr Trp Ala Trp Leu Gly Asp Val Lys
 50                  55                  60

Tyr Ser Leu Ser Phe Thr Ser Arg Tyr His Glu Asn Ser Leu Glu Leu
 65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
        130                 135                 140

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Val Glu Gln Val His Val Ala Ser Trp Pro Ala Met Ser
            180                 185                 190

Pro Leu Gln Pro Asp Val Phe Gln Thr Ser Ile Glu Cys Asn Ala Thr
            195                 200                 205

Val Thr Arg Ser Tyr Ala Ile Glu Gly Gln Thr Phe Val Leu Cys Ser
210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
        290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys Leu Glu Ile
    370

<210> SEQ ID NO 11
<211> LENGTH: 27
<212> TYPE: DNA
<213> ORGANISM: Artificial Sequence
<220> FEATURE:
<223> OTHER INFORMATION: Synthetic primer:G180F

<400> SEQUENCE: 11

```
atgtactccc tgtttgaaca ggtacac                                              27

<210> SEQ ID NO 12
<211> LENGTH: 27
<212> TYPE: DNA
<213> ORGANISM: Artificial Sequence
<220> FEATURE:
<223> OTHER INFORMATION: Synthetic primer:G180L

<400> SEQUENCE: 12
atgtactccc tgcttgaaca ggtacac                                              27

<210> SEQ ID NO 13
<211> LENGTH: 27
<212> TYPE: DNA
<213> ORGANISM: Artificial Sequence
<220> FEATURE:
<223> OTHER INFORMATION: Synthetic primer:G180I

<400> SEQUENCE: 13
atgtactccc tgattgaaca ggtacac                                              27

<210> SEQ ID NO 14
<211> LENGTH: 27
<212> TYPE: DNA
<213> ORGANISM: Artificial Sequence
<220> FEATURE:
<223> OTHER INFORMATION: Synthetic primer:G180V

<400> SEQUENCE: 14
atgtactccc tggttgaaca ggtacac                                              27

<210> SEQ ID NO 15
<211> LENGTH: 27
<212> TYPE: DNA
<213> ORGANISM: Artificial Sequence
<220> FEATURE:
<223> OTHER INFORMATION: Synthetic primer:G180Y

<400> SEQUENCE: 15
atgtactccc tgtatgaaca ggtacac                                              27

<210> SEQ ID NO 16
<211> LENGTH: 27
<212> TYPE: DNA
<213> ORGANISM: Artificial Sequence
<220> FEATURE:
<223> OTHER INFORMATION: Synthetic primer:G180H

<400> SEQUENCE: 16
atgtactccc tgcatgaaca ggtacac                                              27

<210> SEQ ID NO 17
<211> LENGTH: 27
<212> TYPE: DNA
<213> ORGANISM: Artificial Sequence
<220> FEATURE:
<223> OTHER INFORMATION: Synthetic primer:G180N

<400> SEQUENCE: 17
atgtactccc tgaattaaca ggtacac                                              27

<210> SEQ ID NO 18
<211> LENGTH: 27
<212> TYPE: DNA
<213> ORGANISM: Artificial Sequence
```

```
<220> FEATURE:
<223> OTHER INFORMATION: Synthetic primer:G180D

<400> SEQUENCE: 18
atgtactccc tggatgaaca ggtacac                                              27

<210> SEQ ID NO 19
<211> LENGTH: 27
<212> TYPE: DNA
<213> ORGANISM: Artificial Sequence
<220> FEATURE:
<223> OTHER INFORMATION: Synthetic primer:G180C

<400> SEQUENCE: 19
atgtactccc tgtgtgaaca ggtacac                                              27

<210> SEQ ID NO 20
<211> LENGTH: 27
<212> TYPE: DNA
<213> ORGANISM: Artificial Sequence
<220> FEATURE:
<223> OTHER INFORMATION: Synthetic primer:G180R

<400> SEQUENCE: 20
atgtactccc tgcgtgaaca ggtacac                                              27

<210> SEQ ID NO 21
<211> LENGTH: 27
<212> TYPE: DNA
<213> ORGANISM: Artificial Sequence
<220> FEATURE:
<223> OTHER INFORMATION: Synthetic primer:G180S

<400> SEQUENCE: 21
atgtactccc tgagtgaaca ggtacac                                              27

<210> SEQ ID NO 22
<211> LENGTH: 27
<212> TYPE: DNA
<213> ORGANISM: Artificial Sequence
<220> FEATURE:
<223> OTHER INFORMATION: Synthetic primer:A205F

<400> SEQUENCE: 22
acctccatcg agttcaatgc gaccgta                                              27

<210> SEQ ID NO 23
<211> LENGTH: 27
<212> TYPE: DNA
<213> ORGANISM: Artificial Sequence
<220> FEATURE:
<223> OTHER INFORMATION: Synthetic primer:A205L

<400> SEQUENCE: 23
acctccatcg agttgaatgc gaccgta                                              27

<210> SEQ ID NO 24
<211> LENGTH: 27
<212> TYPE: DNA
<213> ORGANISM: Artificial Sequence
<220> FEATURE:
<223> OTHER INFORMATION: Synthetic primer:A205I

<400> SEQUENCE: 24
acctccatcg agataaatgc gaccgta                                              27
```

```
<210> SEQ ID NO 25
<211> LENGTH: 27
<212> TYPE: DNA
<213> ORGANISM: Artificial Sequence
<220> FEATURE:
<223> OTHER INFORMATION: Synthetic primer:A205V

<400> SEQUENCE: 25
acctccatcg aggttaatgc gaccgta                                          27

<210> SEQ ID NO 26
<211> LENGTH: 27
<212> TYPE: DNA
<213> ORGANISM: Artificial Sequence
<220> FEATURE:
<223> OTHER INFORMATION: Synthetic primer:A205Y

<400> SEQUENCE: 26
acctccatcg agtataatgc gaccgta                                          27

<210> SEQ ID NO 27
<211> LENGTH: 27
<212> TYPE: DNA
<213> ORGANISM: Artificial Sequence
<220> FEATURE:
<223> OTHER INFORMATION: Synthetic primer:A205H

<400> SEQUENCE: 27
acctccatcg agcataatgc gaccgta                                          27

<210> SEQ ID NO 28
<211> LENGTH: 27
<212> TYPE: DNA
<213> ORGANISM: Artificial Sequence
<220> FEATURE:
<223> OTHER INFORMATION: Synthetic primer:A205N

<400> SEQUENCE: 28
acctccatcg agaataatgc gaccgta                                          27

<210> SEQ ID NO 29
<211> LENGTH: 27
<212> TYPE: DNA
<213> ORGANISM: Artificial Sequence
<220> FEATURE:
<223> OTHER INFORMATION: Synthetic primer:A205D

<400> SEQUENCE: 29
acctccatcg aggataatgc gaccgta                                          27

<210> SEQ ID NO 30
<211> LENGTH: 27
<212> TYPE: DNA
<213> ORGANISM: Artificial Sequence
<220> FEATURE:
<223> OTHER INFORMATION: Synthetic primer:A205C

<400> SEQUENCE: 30
acctccatcg agtgtaatgc gaccgta                                          27

<210> SEQ ID NO 31
<211> LENGTH: 27
<212> TYPE: DNA
<213> ORGANISM: Artificial Sequence
<220> FEATURE:
<223> OTHER INFORMATION: Synthetic primer:A205R
```

```
<400> SEQUENCE: 31
acctccatcg agcgtaatgc gaccgta                                27

<210> SEQ ID NO 32
<211> LENGTH: 27
<212> TYPE: DNA
<213> ORGANISM: Artificial Sequence
<220> FEATURE:
<223> OTHER INFORMATION: Synthetic primer:A205S

<400> SEQUENCE: 32
acctccatcg agtctaatgc gaccgta                                27

<210> SEQ ID NO 33
<211> LENGTH: 27
<212> TYPE: DNA
<213> ORGANISM: Artificial Sequence
<220> FEATURE:
<223> OTHER INFORMATION: Synthetic primer:A205G

<400> SEQUENCE: 33
acctccatcg agggtaatgc gaccgta                                27
```